United States Patent [19]
Pernetti et al.

[11] Patent Number: 5,692,494
[45] Date of Patent: Dec. 2, 1997

[54] ADJUSTABLE BREATHING CIRCUIT BAG ARM

[75] Inventors: Denise L. Pernetti, Cottage Grove; Terrance P. Sullivan, Madison, both of Wis.

[73] Assignee: Ohmeda Inc., Liberty Corner, N.J.

[21] Appl. No.: 721,367

[22] Filed: Sep. 26, 1996

[51] Int. Cl.$^6$ .................................................. A61M 16/00
[52] U.S. Cl. .................... 128/200.24; 128/202.27; 128/205.13
[58] Field of Search .................. 128/200.24, 202.27, 128/205.13–205.17

[56] References Cited

U.S. PATENT DOCUMENTS

| | | | |
|---|---|---|---|
| 4,020,834 | 5/1977 | Bird | 128/204.25 |
| 4,249,527 | 2/1981 | Ko et al. | 128/204.18 |
| 4,944,292 | 7/1990 | Gaeke et al. | 128/204.18 |
| 5,163,424 | 11/1992 | Koehnke | 128/205.13 |
| 5,195,512 | 3/1993 | Rosso | 128/200.24 |
| 5,220,915 | 6/1993 | Troy et al. | 128/204.25 |
| 5,231,981 | 8/1993 | Schrieber et al. | 128/205.23 |
| 5,259,372 | 11/1993 | Gross et al. | 128/200.24 |
| 5,299,567 | 4/1994 | Joye et al. | 128/204.28 |
| 5,301,667 | 4/1994 | McGrail et al. | 128/205.14 |
| 5,497,766 | 3/1996 | Foster et al. | 128/200.24 |

*Primary Examiner*—Vincent Millin
*Assistant Examiner*—Eric P. Raciti
*Attorney, Agent, or Firm*—Roger M. Rathbun; Salvatore P. Pace

[57] ABSTRACT

A breathing bag arm assembly that is affixed to a medical apparatus such as an anesthesia machine or component thereof. The breathing bag arm assembly comprises three moving parts, a base connector that rotatable attaches to the medical apparatus, a bent tube that is affixed to the base connector and can be rotated to a plurality of discrete locked positions with respect to the base connector and a port connector that is rotatable affixed to the other end of the bent tube. The port connector has a port for connecting to the flexible bag. By manipulation of the assembly, the clinician can locate the flexible bag in a variety of positions for convenient use, and retain the flexible bag in the desired position depending vertically downwardly. The overall assembly is readily disassembled and reassembled for cleaning or the like.

6 Claims, 6 Drawing Sheets

5,692,494

ADJUSTABLE BREATHING CIRCUIT BAG ARM

BACKGROUND OF THE INVENTION

The present invention relates to a medical apparatus, such as an anesthesia machine, and, more specifically, to a breathing bag arm assembly for affixing a breathing bag to the medical apparatus whereby the breathing bag may be manipulated by the user to be positioned in the location desired by the user.

In anesthesia machines marketed today, the machines offer a selection as to how the patient is to be breathed while undergoing anesthesia. Thus, the clinician may elect to breath the patient by the use of a mechanical ventilator that is powered by a variety of means to provide the breath to the patient. Alternatively, the clinician may elect to manually breathe the patient and that is carried out by the use of a flexible breathing bag that the clinician manually compresses to provide a breath to the patient.

Generally a switch is provided for the clinician to make the selection and the switch, as well as the bagging apparatus, is normally conveniently located atop of that part of the medical apparatus or anesthesia machine containing the carbon dioxide absorber.

It is, of course, possible to locate the flexible breathing bag in a variety of locations on the anesthesia machine, however, the positioning of the breathing bag arm assembly, that is, the arm and its various components that attaches the flexible breathing bag to the anesthesia machine, to the head or top of the absorber is quite common. It is also common to locate the switch that allows the clinician to change the system from a mechanical ventilator to the manual bagging mode on the head of the absorber.

Obviously, therefore, it is advantageous for the position and operation of the manually operated flexible breathing bag to be adjustable so that the flexible breathing bag can be reached easily when needed. The clinician may have a personal preference as to the location of the flexible breathing bag and also the position of other equipment surrounding the anesthesia machine may require that the flexible breathing bag be movable to a certain position.

The main functional requirement for the flexible breathing bag and its adjustability is that the bag must communicate through the medical apparatus ultimately to the patient so that the squeezing of the flexible breathing bag by the clinician will cause air to be transmitted to the patient connected to the anesthesia machine to inflate the lungs of that patient.

Accordingly, the breathing bag arm assembly must provide a passageway that allows the flexing of the bag to force air into the patient through other parts of the anesthesia machine. Along with that requirement is the need for the flexible breathing bag itself to be vertically positionable, that is, whatever manipulations are done to the flexible breathing bag and its mounting assembly, it is ultimately desirable that the flexible breathing bag be positioned in a vertical position such that it hangs down vertically from its mounting so that it can be easily manipulated by the clinician.

As a further desirable feature, the entire breathing bag arm assembly must be readily disassembled so that all of the components may be easily cleaned, by scrubbing and/or the entire assembly can be sterilized in an autoclave apparatus.

As a preference, it is also advantageous that the flexible breathing bag be capable of being adjusted to the desired position by the clinician and that position maintained, that is, that the bag is in a relatively set or permanent position until the clinician desires to again relocate the flexible breathing bag to another position.

SUMMARY OF THE INVENTION

The adjustable breathing bag arm assembly of the present invention is readily and conveniently adjusted to a variety of positions by the clinician to locate the flexible breathing bag in the most convenient position to manually operate the bag. By combining a base connector, an intermediate bent tube and a port connector, the components of the present breathing bag arm assembly are easily disassembled for cleaning. The three components are all movable and therefore considerable flexibility is provided to relocate the flexible breathing bag to a desired position.

The base connector is affixed to the particular piece of medical apparatus that is a part of the overall anesthesia machine. In the preferred embodiment, the apparatus is the head of the absorber system and is positioned near the clinician. The base connector is rotatable with respect to the absorber head.

The intermediate bent tube is rotatably connected to the base connector so that it can be rotated, preferably, to a plurality of discrete positions and in each instance, the movement to a different position is easy to facilitate and the intermediate bent tube is quickly locked into the particular selected angular position without the need to untighten and retighten locking bolts. As a further feature, the intermediate bent tube is formed at various angles, that is, the intermediate section of the tube has a longitudinal axis that is at an angle to the axes of the ends of the bent tube.

Finally, the port connector is affixed to the free end of the intermediate bent tube and is rotatable to a full circle at that end. A port is provided on the port connector so that the flexible breathing bag, when attached to the port, can always hang vertically downward for the convenience of the clinician as well as to meet certain international standards.

Accordingly, with few parts, all of which are easily disassembled for cleaning or autoclaving, the breathing bag arm assembly of the present invention can be adjustable to a position convenient to the clinician with minimum of effort, can be locked into the desired position and allow the flexible breathing bag to be connected where it descends downwardly vertically.

DESCRIPTION OF THE PREFERRED EMBODIMENT

Figure 1:
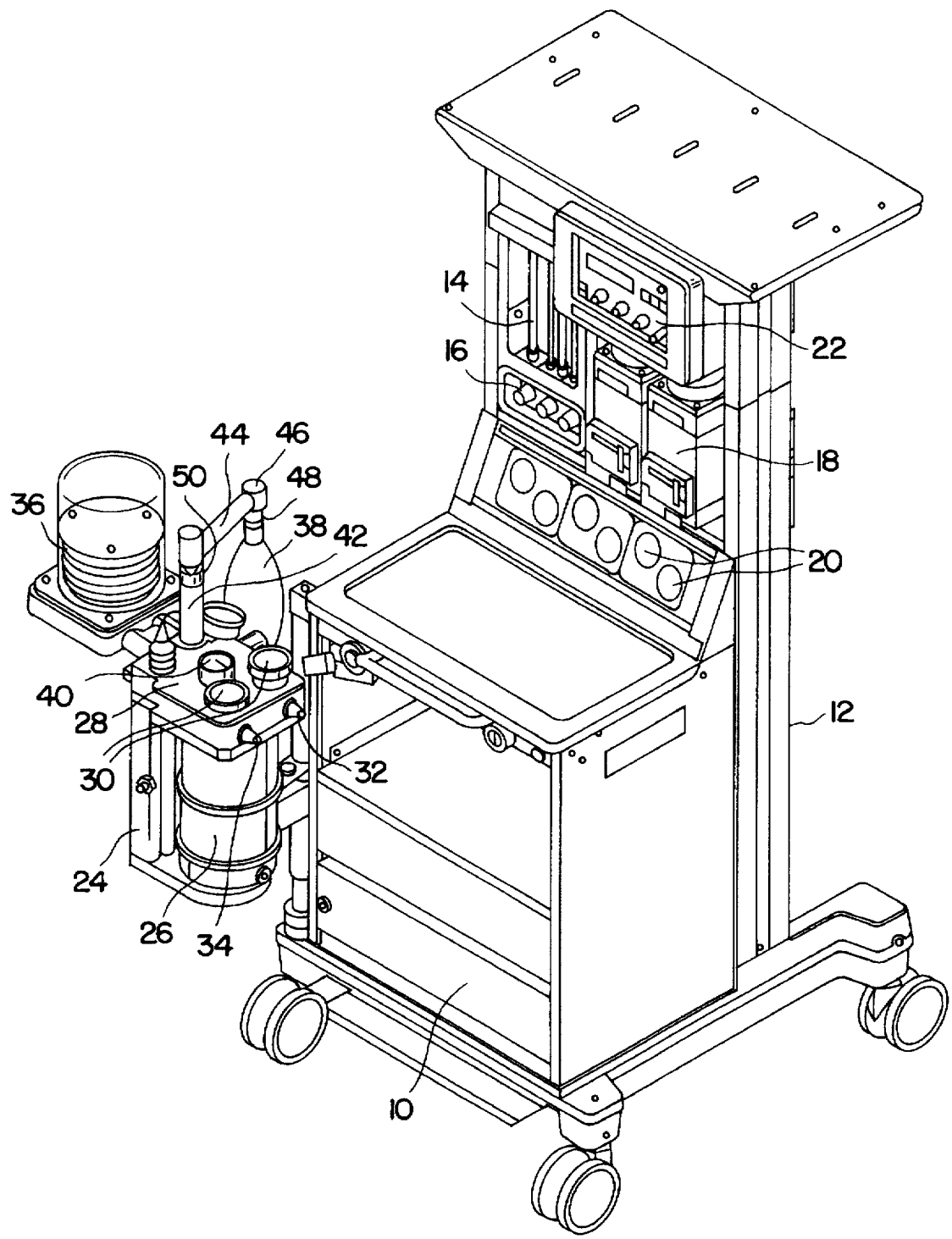
FIG. 1 is an isometric view of an anesthesia machine including a breathing bag arm assembly currently in use in the prior art.

Referring now to FIG. 1, there is shown an isometric view of an anesthesia machine 10 having a breathing bag arm assembly constructed in accordance with the prior art. The anesthesia machine 10 is a currently marketed product of Ohmeda Inc. and includes a frame 12 to support the various equipment such as flow tubes 14 with flow control valves 16 to adjust and control the various gases incoming to the machine and to create the desired flow and mixtures of those gases. Vaporizers 18 are included to vaporize a volatile liquid anesthetic for introduction into the flow of gases to the patient to anesthetize that patient. Various other components are included such as pressure gauges 20 to monitor various pressures in the system and a ventilator control module 22 to set the mechanical ventilator to the desired parameters, such as tidal volume, minute flow etc. of the gases to be supplied to the patient.

Also affixed to the frame 12 is a carbon dioxide absorber assembly 24 which includes a carbon dioxide absorber 26 to rid the recirculating gases from the patient of carbon dioxide so that some of the same expired gases can be reintroduced to the patient. Typically, the $CO_2$ absorber assembly 24 includes a absorber head 28 that contains various other components of the overall anesthesia machine. Such additional components include check valves 30 to allow flow in the proper direction to and from the patient, and an inlet and outlet 32,34 for providing a breathing gas to and from, respectively, the patient breathing circuit.

Also shown connected to the absorber head 28 is a bellows container 36 that contains a bellows that cooperates with a mechanical ventilator to provide powered breaths to the patient. Alternatively a flexible breathing bag 38 is included and which can be manually squeezed or contracted by the clinician to provide that breath to the patient. A switch 40 is conveniently located on the absorber head 28 for the clinician to select between using a mechanical ventilator to breathe the patient or manually manipulate the flexible breathing bag 38. As can be seen, obviously when the flexible breathing bag 38 is used, it needs to be in a convenient position so that the clinician operating the anesthesia machine 10 can easily reach the flexible breathing bag 38 while attending to various other functions of the anesthesia machine. The flexible breathing bag 38, therefore, must be in a convenient location and be adjustable in its position for various preferences of the clinician or due to the constraints of other equipment associated with the anesthesia machine 10.

In the anesthesia machine of FIG. 1, the flexible breathing bag 38 is affixed to the absorber head 28 by means of a adjustable breathing bag arm assembly including a vertical tube 42 and horizontal tube 44 communicating with each other. The horizontal tube 44 has a end connector 46 that provides a port 48 for actual connection to the flexible breathing bag 38 that extends downwardly in a vertical direction for ease of use by the clinician.

In the prior art breathing bag arm assembly of FIG. 1, a vertical adjustment of the position of the flexible breathing bag 38 is accomplished by a telescoping arrangement of the vertical tube 42 such that an upper portion can be raised or lowered by the clinician to adjust the vertical position of the flexible breathing bag 38. When the telescoping vertical tube 42 has been so positioned, the clinician tightens a nut 50 to secure the vertical tube 42 in the desired position.

It is clear that some repositioning of the flexible breathing bag 38 is therefore possible by the clinician, however, that positioning is quite limited and a manual loosening and retightening of a nut 50 is necessary for each change of position.

Figure 2:
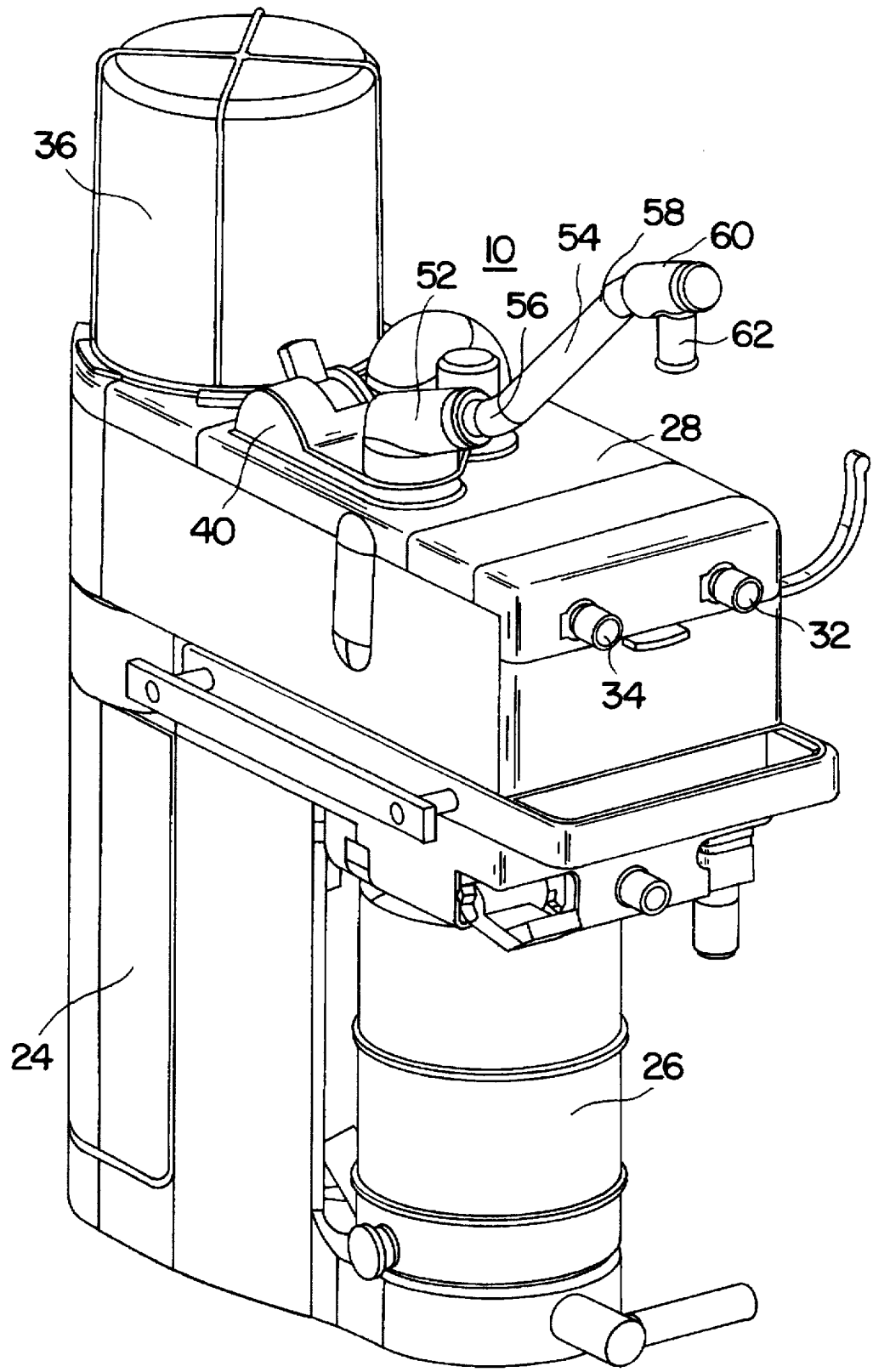
FIG. 2 is an isometric view of a part of the anesthesia machine of FIG. 1 having the breathing bag arm assembly constructed in accordance with the present invention.

Turning now to FIG. 2, there is shown an isometric view of a part of the anesthesia machine 10 having the flexible breathing bag arm assembly constructed in accordance with the present invention. In FIG. 2, like numbers have been assigned to components described with respect to FIG. 1 even though the actual parts may appear different, however, the breathing bag arm assembly will be described in more detailed as it relates directly to the invention disclosed herein.

As shown therefore in FIG. 2, the breathing bag arm assembly is mounted atop the absorber head 28 and includes a base connector 52 that is mounted to that absorber head 28 as will be explained. As will become clear, the base connector 52 is rotatably mounted to the absorber head 28 and can be manually rotated by the user. Affixed to the base connector 52 is a bent tube 54 and, again, as will be described, the bent tube 52 includes a proximal end 56 that is affixed to the base connector 52 in a manner that it is rotatable therewith in discrete finite lockable rotated positions. At the distal end 58 of the bent tube 54 there is a port connector 60 that, again is rotatably mounted to the bent tube 54 in a manner to be described. Extending downwardly from the port connector 60 is a port 62 that is provided for the connection to the breathing bag, not shown in FIG. 2 but is mounted in the manner as shown in FIG. 1.

Figure 3:
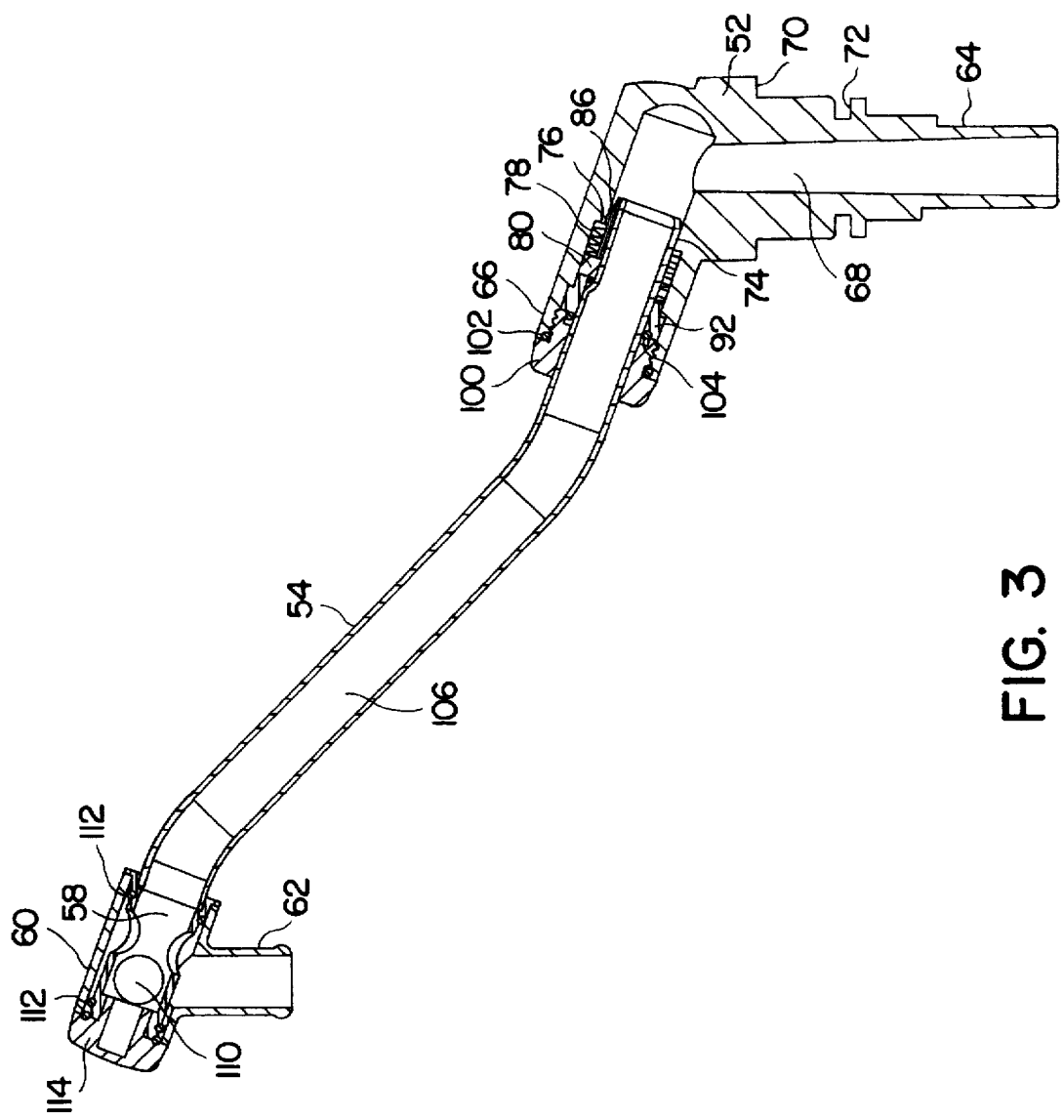
FIG. 3 is a side cross sectional view of the flexible bag arm assemble in accordance with the present invention.
Figure 4:
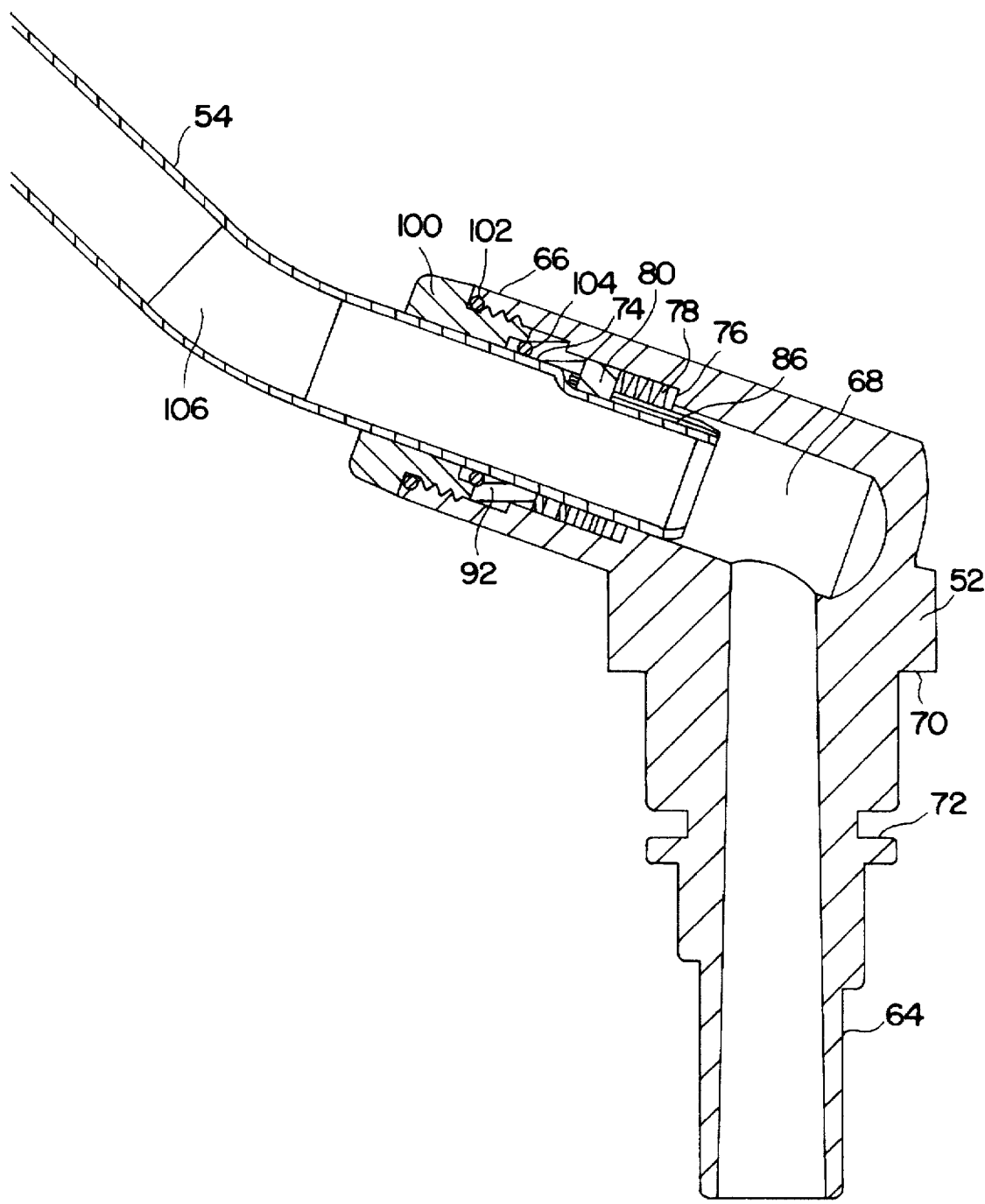
FIG. 4 is an enlarged side cross sectional view of one of the components of the assembly of FIG. 3, FIGS. 5A and 5B are isometric views of two of the components used in the subject invention.

Turning now to FIGS. 3 and 4, there is shown, respectively, a side cross sectional view of the breathing bag arm assembly constructed in accordance with the present invention and an enlarged side cross sectional view of one of the components of the breathing bag arm assembly.

In FIGS. 3 and 4, the base connector 52 has a proximal end 64 and a distal end 66 and a passageway 68 that passes between the proximal end 64 and the distal end 66 to convey fluid therebetween. As used in the description, the proximal end of any of the components will be described as the end toward the absorber head 28 and therefore the distal ends are those extending outwardly from the absorber head 28.

Thus, the proximal end 64 of the base connector 52 fits within the absorber head 28 or, as indicated, some other piece of medical apparatus associated with the anesthesia machine. A flange 70 seats against the upper surface of the absorber head 28 and a groove 72 is provided so that the base connector 52 can be secured to the absorber head 28 by means such as a C-clip, not shown. Therefore, the passageway 68 can communicate with a passage within the carbon dioxide absorber assembly 24 to provide a communication with the patient as is conventional. By the seating of the base connector 52 into the medical apparatus by means of a C-clip, the base connector 52 is readily rotatable with respect to the particular piece of medical apparatus again in conventional manner. In the preferred embodiment, the flexible breathing bag 38 may be rotated about 240 degrees about a vertical axis, however, the degree of rotation may depend upon the needs of the user and the proximity of other obstructions to the movement of the flexible breathing bag 38 and its associated connections.

At the distal end 66 of the base connector 52, there is secured to the bent tube 54 such that it may be rotated with respect to the base connector 52 to a plurality of discrete positions and locked into any one of the selected positions.

Figure 5A:
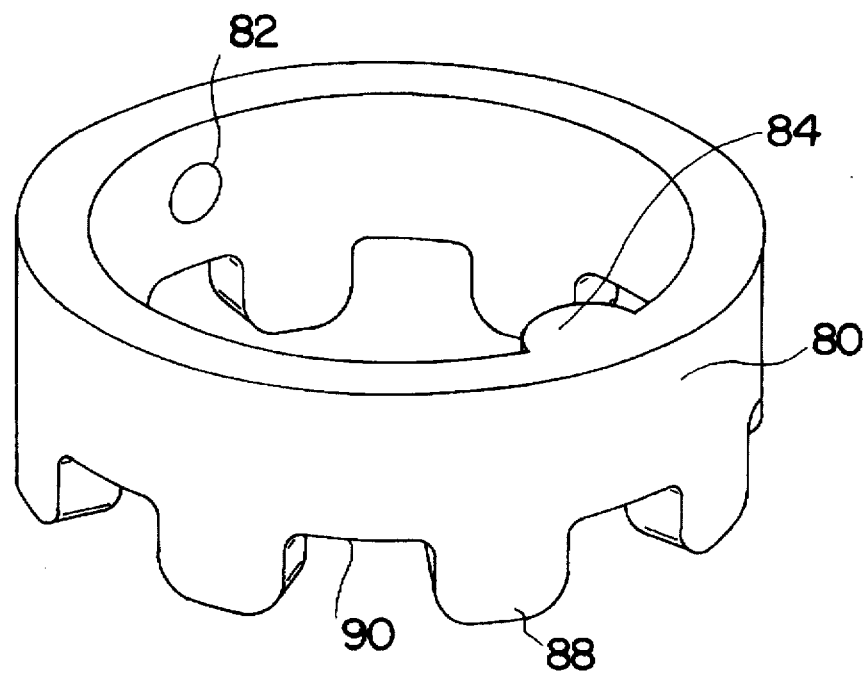

As shown, the proximal end 74 of bent tube 54 interfits within the distal end 66 of base connector 52. An annular ridge 76 is formed in the interior of the distal end 66 of base connector 52 and which forms a seat for a spring 78. At the proximal end of bent tube 54, a locking gear 80 is secured, and is more clearly shown in FIG. 5A. The locking gear 80 may be secured to the proximal end 74 on the bent tube 54 by means such as a set screw (not shown) through a hole 82 and the locking gear 80 can be further prevented from rotating on the proximal end 74 of bent tube 54 by a key 84 that slides in a suitable groove 86 in the proximal end 74.

As shown in FIGS. 3 and 4 again, the spring 78 thus is positioned and compressed between the locking gear 80 and the annular ridge 74 to provide a bias in the outward direction against the proximal end 74 of the bent tube 54. The locking gear 80 has a plurality of teeth 88 and recesses 90 therebetween, the purpose of which will become apparent.

Figure 5B:
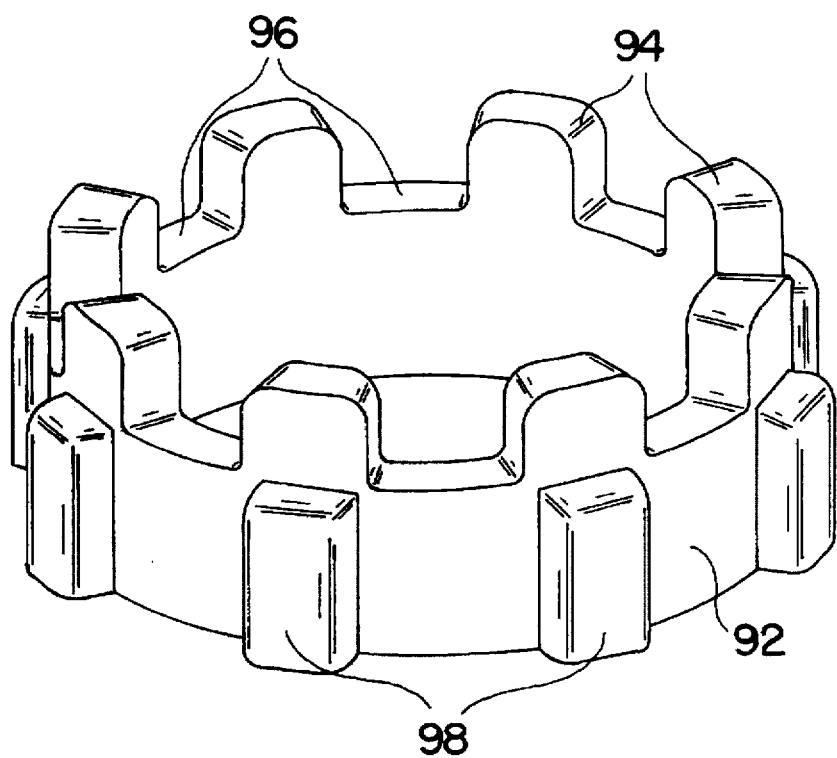

Another locking gear 92 is fitted within and secured to the distal end 66 of the base connector 52 and is more clearly shown in FIG. 5B. The locking gear 92 also has a plurality of teeth 94 and recesses 96 and also has means to prevent the locking gear 92 from rotating within the distal end 66 of base connector 52. As shown in FIG. 5B, that means may be a plurality of protrusions 98 that interfit with corresponding grooves formed in the interior of the distal end 66 so that the locking gear 92 can be slid into position and will not rotate.

A locking nut 100 retains the proximal end 74 of the bent tube 54 in position on the distal end 66 of base connector 52 and is threadedly engaged to the distal end 66. Suitable O-rings 102 and 104 are provided to seal, respectively, the exterior and interior surfaces of locking nut 100 to prevent fluid from leaking from passageway 68 of base connector 52 or from the passageway 106 in bent tube 54.

As can now be seen, when the locking nut 100 secures the bent tube 54 in position affixed to the base connector 52, the bent tube 54 is spring biased outwardly by the spring 78 and the locking gear 80 on the base connector 52 is engaged with the locking gear 92 on the bent tube 54. Therefore at that position, the bent tube 54 cannot be rotated with respect to the base connector 52.

When it is desired to rotate the bent tube 54 to a different position with respect to the base connector 52, the clinician merely needs to push on the bent tube 54 in the direction toward the base connector 52 to disengage the locking gears 80 and 92 since the movement of the bent tube 54 against the spring 78 allows the teeth 88 and 94 to disengage each other. At that point, the clinician can rotate the bent tube 54 to the desired position and release the bent tube 54 where the spring 78 will return it to the engaged position where each locking gear reengages the other.

Accordingly, as can be seen, in the embodiment shown, there are eight teeth on each of the locking gears 80, 92 and thus the bent tube 54 may be repositioned to any one of eight positions at spaced angles of 45 degrees rotation. Obviously, any of a variety of differing numbers of teeth and spacing may be employed to vary the rotational positions of the bent tube 54 within the spirit of the present invention.

Taking now, the distal end 108 of the bent tube 54, the port connector 60 is rotatably affixed thereto. The passageway 106 in bent tube 54 includes a number of openings 110 for the fluid within passageway 106 to enter the port connector 60 and pass through port 62 to the flexible breathing bag (not shown). The port connector 60 is sealed for the passage of such fluid by a pair of O-rings 112 and an end cap 114 is screwed into the distal end of the bent tube 54 to secure the port connector 60 to the bent tube 54.

Figure 6:
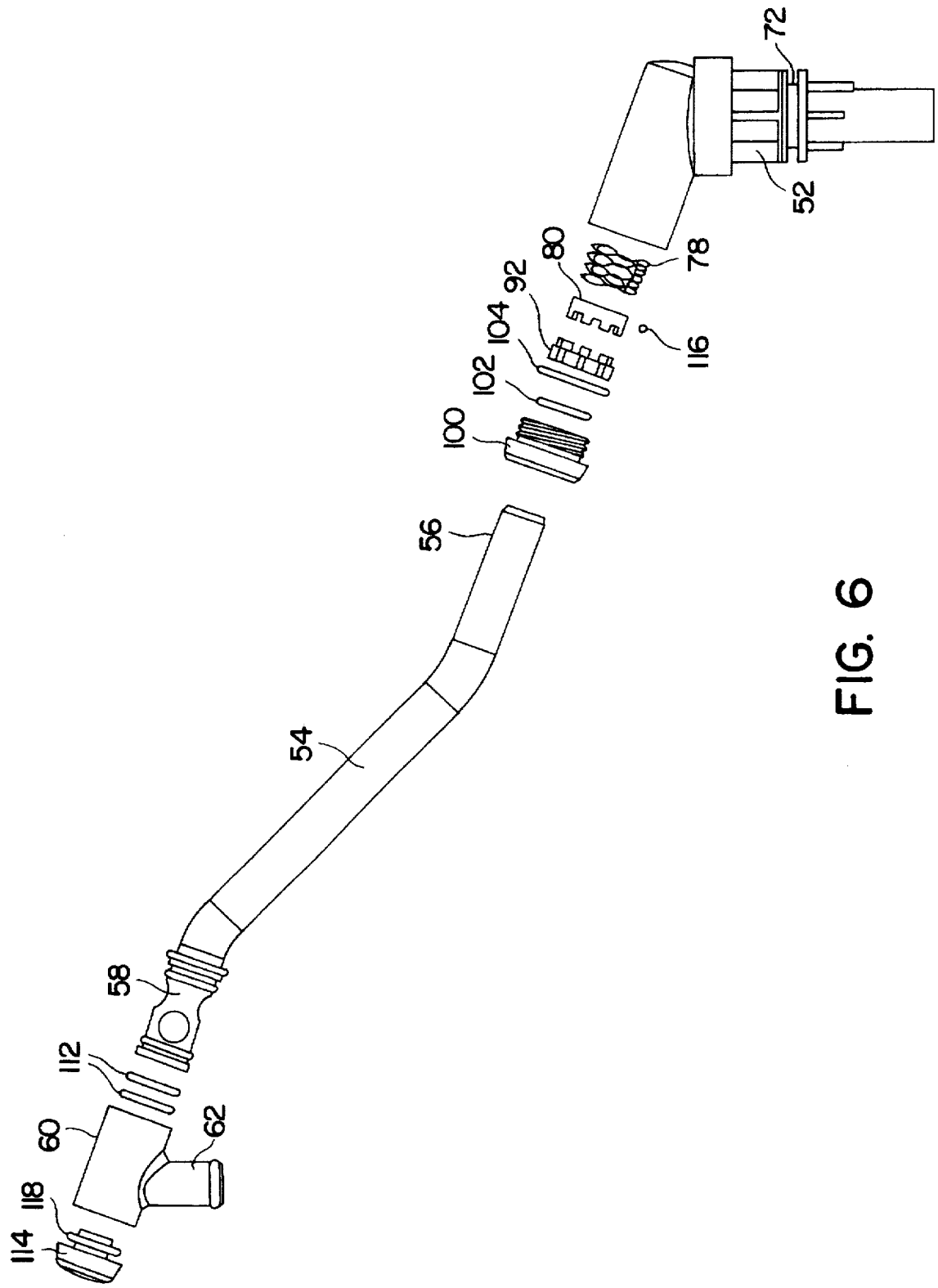
FIG. 6 is an exploded view of the overall breathing bag arm assembly of the present invention.

Finally, turning to FIG. 6, there is shown an exploded view of the breathing bag arm assembly constructed in accordance with the present invention and which illustrates the ease by which the apparatus can be assembled and disassembled for cleaning. As shown, the apparatus is easily removed from the medical apparatus by simply removing the C-ring that retains it to the apparatus within the groove 72. The bent tube 54 is easily separated from the base connector 52 by unscrewing the locking nut 100 and removing the bent tube 54 along with O-rings 102, 104 and the locking gear 92 captured. With that simple operation, the bent tube 54 with the locking gear 80 affixed there to by the set screw 116 is removable as well as the spring 78.

Removal of the port connector 60 is as easily accomplished by unscrewing the end cap 114 such that its O-ring 118 is removed and the port connector 60 can be slipped off the distal end 58 of bent tube 54 for cleaning or the like. The O-rings 112 are thus readily replaced.

Accordingly, the overall breathing bag arm assembly of the present invention allows considerably flexibility in positioning the flexible breathing bag within the desired location by the clinician by relatively simple means that is easy to disassemble for cleaning, replacement and the like.

While the present invention has been set forth in terms of a specific embodiment, it will be understood that the anesthesia system herein disclosed may be modified or altered by the those skilled in the art to other configurations. Accordingly, the invention is to be broadly construed and limited only by the scope and the spirit of the claims appended hereto.

We claim:

1. A breathing bag arm assembly for attaching a flexible breathing bag to a medical apparatus to provide a fluid connection between a flexible breathing bag through a conduit within a medical apparatus to a patient, said assembly comprising:

a base connector, said base connector having a proximal end rotatably affixed to a medical apparatus, a distal end and fluid passageway communicating between said distal end and said proximal end, a bent tube having a distal end and a proximal end, said proximal end having a longitudinal axis, said proximal end being rotatably affixed to said distal end of said base connector to be rotatable about said longitudinal axis to a plurality of discrete, rotatably locked positions, said bent tube having a fluid passageway therethrough communicating with said fluid passageway in said base connector, a port connector rotatably affixed to the distal end of said bent tube, said port connector having a port adapted to be connected to a flexible breathing bag, said port being rotatable to a downward position when said port connector is rotated with respect to said distal end of said bent tube.

2. A breathing bag arm assembly as defined in claim 1 wherein said bent tube has a longitudinal axis for its distal end and its proximal end and includes an intermediate section between said distal end and said proximal end, wherein said intermediate section has a longitudinal axis formed at an angle to each of said longitudinal axes of said distal and proximal ends.

3. A breathing bag arm assembly as defined in claim 1 wherein said rotatable connection between said proximal end of said bent tube and said base connector comprises a pair of interconnectable locking gears movable laterally along said longitudinal axis to disconnect said interconnection and to reestablish said interconnection when said bent arm has been rotated to the desired position.

4. A breathing bag arm assembly as defined in claim 3 wherein said interconnectable locking gears are biased along said longitudinal axis to establish said interconnection with respect to each other.

5. A breathing bag arm assembly as defined in claim 4 wherein said interconnectable locking gears are rotatable with respect to each other to a plurality of discrete radial positions.

6. A breathing bag arm assembly as defined in claim 5 wherein said plurality of discrete positions are angles of about 45 degrees.

* * * * *